US00PP28988P2

(12) United States Plant Patent
Noack

(10) Patent No.: US PP28,988 P2
(45) Date of Patent: Feb. 27, 2018

(54) SHRUB ROSE PLANT NAMED 'NOA1811108'

(50) Latin Name: *Rosa hybrida*
Varietal Denomination: Noa1811108

(71) Applicant: Reinhard Noack, Gutersloh (DE)

(72) Inventor: Reinhard Noack, Gutersloh (DE)

( * ) Notice: Subject to any disclaimer, the term of this patent is extended or adjusted under 35 U.S.C. 154(b) by 0 days.

(21) Appl. No.: 15/530,436

(22) Filed: Jan. 13, 2017

(51) Int. Cl.
*A01H 5/02* (2006.01)

(52) U.S. Cl.
USPC ..... Plt./107

(58) Field of Classification Search
USPC ..... Plt./107
CPC ..... A01H 5/0222
See application file for complete search history.

*Primary Examiner* — Kent L Bell
(74) *Attorney, Agent, or Firm* — Cassandra Bright

(57) ABSTRACT

A new and distinct shrub rose cultivar, for garden use named 'Noa1811108' is disclosed, characterized by full, double, medium pink flowers with fragrance and strong peduncles. Plants have excellent resistance to blackspot, powdery mildew, downy mildew and rust diseases. The foliage is very glossy and it contrasts well to the pink flowers. The new variety is a hybrid shrub rose, normally produced as an outdoor garden or container plant.

2 Drawing Sheets

Figure 1:
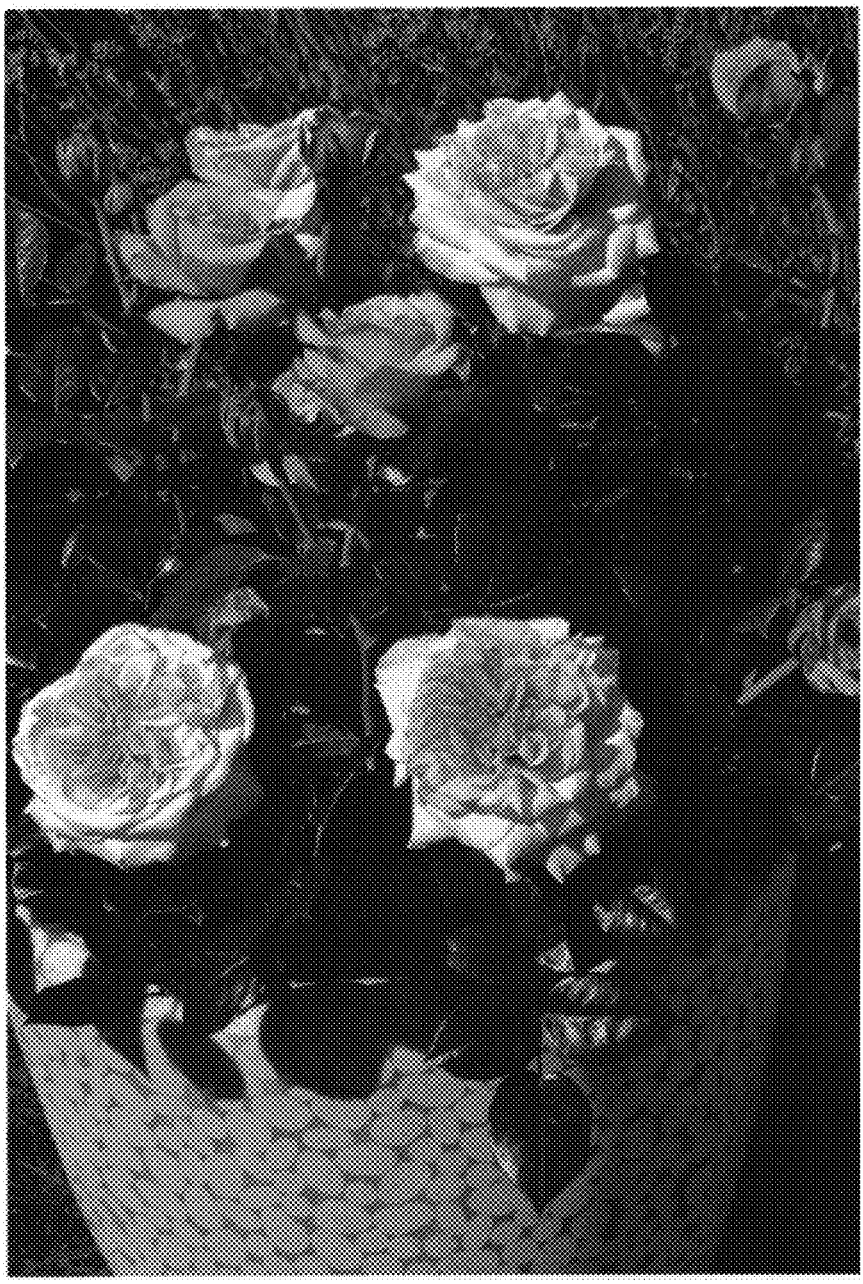

Latin name of the genus and species: *Rosa hybrida.*
Variety denomination: 'Noa1811108'.

BACKGROUND OF THE INVENTION

The new *Rosa* cultivar is a product of a planned breeding program conducted by the inventor, Reinhard Noack, conducted in Gutersloh, Germany. The objective of the breeding program was to create new and distinct shrub rose plants with unique qualities such as, uniform growth and full flowering in combination with fragrance. The inventor also sought to produce plants with profuse, full flowers with strong peduncles, attractive, abundant foliage, as well as excellent resistance to diseases encountered in landscapes and gardens and strong reblooming. These objectives have been substantially achieved and in that distinguish 'Noa1811108' from all other varieties of which the inventor is aware. This combination of qualities is not present in prior rose cultivars known to the inventor. The cross resulting in this new variety was made during April of 2008.

The seed parent is the unpatented, commercial variety *Rosa* 'Charisma'. The pollen parent is an unpatented, unnamed proprietary *Rosa hybrida*. The new variety was discovered in April of 2009 by the inventor in a group of seedlings resulting from the 2008 crossing, in a research greenhouse in Gutersloh, Germany.

Asexual reproduction of the new cultivar was performed by terminal semi-soft wood vegetative cuttings. This was first performed at a research greenhouse in Gutersloh, Germany in Summer of 2010 and has shown that the unique features of this cultivar are stable and reproduced true to type in successive generations.

SUMMARY OF THE INVENTION

The cultivar 'Noa1811108' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Noa1811108' These characteristics in combination distinguish 'Noa1811108' as a new and distinct *Rosa* cultivar:

1. Pink flower color near Red 55A and 55C.
2. Full, double flowers.
3. Plants have excellent resistance to blackspot, powdery mildew, downey mildew and rust diseases.
4. Fragrant flowers.
5. Strong peduncle.

Plants of the new cultivar 'Noa1811108' are similar to plants of the seed parent, in most horticultural characteristics, however, plants of the new cultivar 'Noa1811108' differ in the following:

1. The new variety has pink flowers, 'Charisma' has red-pink flowers.
2. While both varieties are double flowering, new variety has a fuller flower, with more petals.
3. Growth habit of the new variety is shrubby, the growth habit of 'Charisma' is upright.

Plants of the new cultivar 'Noa1811108' are similar to plants of the pollen parent in most horticultural characteristics, however, plants of the new cultivar 'Noa1811108' differ in the following;

1. The new variety has pink flowers, the pollen parent has red flowers.
2. Flowers of the new variety are double and very full, flowers of the pollen parent are semi-double.
3. Flowers of the new variety are fragrant, flowers of the pollen parent have no fragrance.

COMMERCIAL COMPARISON

Plants of the new cultivar 'Noa1811108' can be compared to the commercial variety *Rosa* 'Noa1112130', filed concurrently, (U.S. Plant patent application Ser. No. 15/530, 435). These varieties are similar in most horticultural characteristics; however 'Noa1811108' differs in the following:

1. The new variety has pink flowers, this comparator has creamy pastel yellow-orange petals.
2. Flowers of 'Noa1811108' typically have 80 to 90 petals, flowers of 'Noa1112130' typically have 60 to 65 petals.
3. Plants of 'Noa1811108' are approximately 70-90 cm in height, plants of 'Noa1112130' are typically 110 cm in height.

Plants of the new cultivar 'Noa1811108' can be compared to the commercial variety *Rosa* 'Noa38121', filed concurrently, (U.S. Plant patent application Ser. No. 15/530,424). These varieties are similar in most horticultural characteristics; however 'Noa1811108' differs in the following:

1. The new variety has pink flowers, this comparator has much darker pink (red-purple) flowers.
2. Flowers of 'Noa1811108' typically have 80 to 90 petals, flowers of 'Noa38121' typically have 60 to 65 petals.
3. The leaves of the new variety are very glossy, the leaves of 'Noa38121' are matte.

BRIEF DESCRIPTION OF THE PHOTOGRAPHS

The accompanying photograph in FIG. 1 illustrates in full color a typical plant of 'Noa1811108'. Age of the plant photographed is approximately 3 years.

Figure 2:
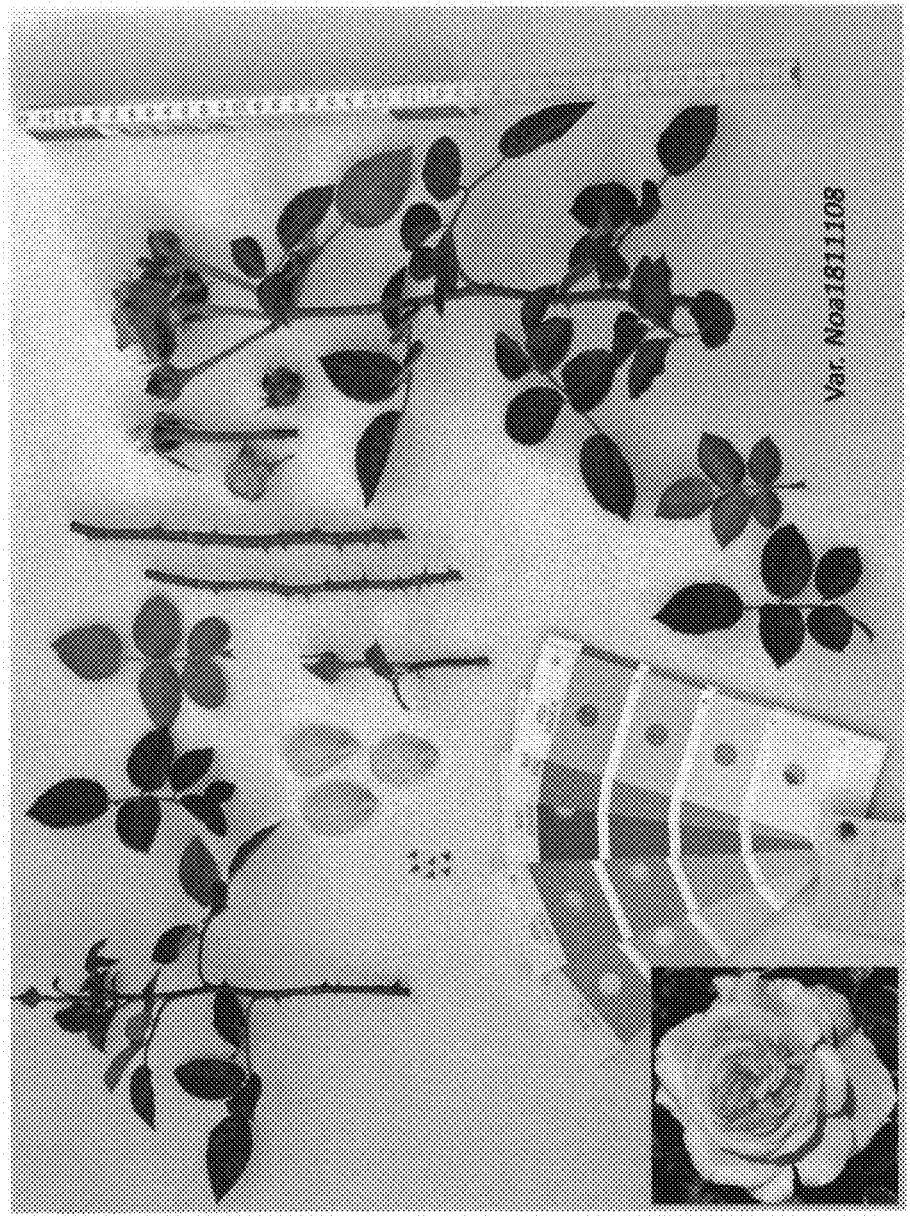

FIG. 2 illustrates a close up of a detailed view of a flower, bud, stem, thorns, petals, foliage together with a color chart for flower color reference.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'Noa1811108' plants grown outdoors, in Gutersloh, Germany. The growing temperature ranged from approximately −1° C. to 35° C. during the day and from approximately −16° C. to 20° C. during the night. General light conditions are bright, normal sunlight. Measurements and numerical values represent averages of typical plant types.

Botanical classification: *Rosa* 'Noa1811108'.

Commercial classification: Shrub rose.

PROPAGATION

Time to initiate roots: About 42 days at approximately 20° C.

Time to produce a rooted cutting: About 90 days at approximately 15° C.

Root description: Fibrous roots.

PLANT

Age of plant described: Approximately 3 years, planted in the ground.

Growth habit: Shrubby, semi-upright.

Height: Average range 70 to 90 cm.

Plant spread: 50 cm.

Rootstock: Own root.

Growth rate: Approximately 40 to 50 cm per year.

Branching characteristics: Sympodial branching.

Length of primary lateral branches: Average 50 cm.

Diameter of lateral branches: Approximately 6 mm.

Quantity of lateral branches: Approximately 5-7.

Branching arrangement: Alternate.

Branches:

Young wood:

*Diameter*.—Approximately 3 to 4 mm.

*Texture*.—Glabrous.

*Approximately density/quantity of thorns*.—Low density.

*Color*.—Near Red 47A.

Branches:

Old wood:

*Diameter*.—Approximately 1.5 cm, after 3 years.

*Color*.—Near Green RHS 143D, with brown tinge not accurately described with R.H.S. chart.

*Texture*.—Smooth.

*Approximately density/quantity of thorns*.—Approximately 10 to 12 per 10 cm stem.

*Color of thorns*.—Young: Near Greyed-Red 180A. Mature: Near Greyed-Purple 184A.

*Size and shape of thorns*.—Typical deltate thorn, approximately 5 to 10 mm in height and 5 mm at base.

FOLIAGE

Leaf:

*Arrangement*.—Alternate.

*Quantity*.—Approximately 30 to 35 per main branch.

*Average length*.—Approximately 10 cm.

*Average width*.—Approximately 8 cm.

Leaflet:

*Quantity*.—Approximately 5 to 7 per leaf.

*Average length*.—Approximately 4 cm.

*Average width*.—Approximately 2.0 cm.

*Shape of blade*.—Ovate.

*Apex*.—Acute.

*Base*.—Obtuse.

*Margin*.—Serrated.

*Appearance of top surface*.—Highly glossy.

*Appearance of bottom surface*.—Matte.

*Texture of top surface*.—Non-pubescent.

*Texture of bottom surface*.—Non-pubescent.

*Leaf internode length*.—Average 3 to 4 cm.

*Color*.—Young foliage upper side: Near Green RHS 138A. Young foliage under side: Near Green RHS 138B. Moderate anthocyanin flushing Red-Purple 58A. Mature foliage upper side: Near Green RHS 138A. Mature foliage under side: Near Green RHS 138B.

*Venation*.—Type: Pinnate. Venation color upper side: Near Green 138A. Venation color under side: Near Yellow-Green 150A.

Petiole:

*Average length*.—Approximately 2 cm.

*Average diameter*.—Approximately 5 mm.

*Color*.—Near RHS Greyed-Red 178A.

*Texture*.—Glabrous, matte.

Rachis:

*Average length*.—Average range 6.0 to 8.0 cm.

*Average diameter*.—Approximately 5 mm.

*Texture*.—Glabrous.
*Color*.—Near RHS Greyed-Red 178A.

Stipule:
*Average length*.—Average 1.0 cm.
*Average diameter*.—Approximately 5 mm.
*Texture*.—Glabrous. Highly glossy.
*Color*.—Near RHS Green 138A, flushed with anthocyanin Red-Purple 58A.

FLOWER

Natural flowering season: Spring until mid-Fall.
Begins flowering after how many years/months: As early as 3 months from a rooted liner.
Flower type and habit: Fully double flowers, occurring 2 to 3 per flowering node.
Rate of flower opening: Approximately 7 day from bud to fully opened flower.
Flower longevity on plant: 6 to 8 days after fully opened.
Individual flower size:
*Diameter*.—Approximately 10 to 12 cm.
*Depth*.—Approximately 3 to 4 cm.

Peduncle:
*Length*.—6 cm.
*Diameter*.—1 cm.
*Texture*.—Glabrous.
*Color*.—Near RHS Green 138B.

Petals:
*Petal arrangement*.—Formal, rotate, overlapping.
*Size*.—Length: Average 3 to 4 cm. Width: Average 2 to 3 cm.
*Shape*.—Obovate.
*Margin*.—Entire, non-ruffled.
*Apex*.—Obtuse, rounded.
*Base*.—Attenuate.
*Petal quantity*.—Average range 80 to 90.
*Texture*.—Smooth.

Color:
*Petals*.—When opening: Upper surface: Near RHS Red 55A. Lower surface: Near RHS Red 55A, base near Yellow-Orange 19A. Fully opened: Upper surface: Near RHS Red 55C. Lower surface: Near RHS Red 55C, base near Yellow-Orange 19A. Color Changes when aging: Fades in very hot weather.

Bud:
*Shape*.—Broad ovate.
*Length*.—Approximately 2.5 cm.
*Diameter*.—Approximately 2 cm.
*Color*.—Near Red 55A.

Sepals:
*Length*.—1.5 cm.
*Width*.—1.0 cm.
*Shape*.—Lanceolate.
*Color*.—Interior Surface: Near RHS Yellow-Green 147C. Exterior Surface: Near RHS Yellow-Green 147B.
*Texture*.—Densely puberulent interior and exterior surfaces.
*Sepal extensions*.—Weak.
*Quantity*.—Average 5 per flower.

Receptacle:
*Length*.—1.0 cm.
*Width*.—1.5 cm.
*Shape*.—Pitcher shaped.
*Color*.—Near RHS Green 143A.

Fragrance: Moderately strong.

REPRODUCTIVE ORGANS

Stamens:
*Number*.—Approximately 30-40.
*Filament length*.—Approximately 5 mm.
*Filament color*.—Light yellow, not accurately determined with R.H.S. colour chart.

Anthers:
*Length*.—1 mm.
*Shape*.—Narrow ovate.
*Color*.—Near Greyed-Orange 166A.
*Pollen*.—Color: Near Yellow 15A. Quantity: Abundant.

Pistil:
*Number*.—Approximately 10-15.
*Pistil length*.—Approximately 4 mm.
*Style*.—Length: Approximately 2 mm. Color: Light green to cream, not accurately determined with R.H.S. chart.
*Stigma*.—Shape: Linear. Color: Light green to cream, not accurately determined with R.H.S. chart.

OTHER CHARACTERISTICS

Seeds and fruits: Not observed to date. Fruits typically dry up, without fully forming.
Disease/pest resistance: Excellent resistance to blackspot, powdery mildew, downy mildew and rust. Average resistance to normal pests of garden roses.

What is claimed is:

1. A new and distinct shrub rose plant named 'Noa1811108' as herein illustrated and described.

* * * * *